(12) United States Patent
Lee (10) Patent No.: US 11,289,302 B2
(45) Date of Patent: Mar. 29, 2022

(54) CERAMIC SHIELDING APPARATUS

(71) Applicant: Han Sung Lee, Hwaseong-si (KR)

(72) Inventor: Han Sung Lee, Hwaseong-si (KR)

( * ) Notice: Subject to any disclaimer, the term of this patent is extended or adjusted under 35 U.S.C. 154(b) by 0 days.

(21) Appl. No.: 16/937,828

(22) Filed: Jul. 24, 2020

(65) Prior Publication Data

US 2021/0066018 A1    Mar. 4, 2021

(30) Foreign Application Priority Data

Jul. 24, 2019   (KR) .................. 10-2019-0089615

(51) Int. Cl.
| | |
|---|---|
| H01J 37/18 | (2006.01) |
| H01J 35/16 | (2006.01) |
| H01J 35/12 | (2006.01) |
| G21F 3/00 | (2006.01) |
| G21F 7/00 | (2006.01) |
| G21F 1/06 | (2006.01) |
| H01J 35/18 | (2006.01) |
| H01J 35/08 | (2006.01) |

(52) U.S. Cl.
CPC ............ *H01J 35/18* (2013.01); *G21F 3/00* (2013.01); *G21F 7/00* (2013.01); *H01J 35/112* (2019.05); *H01J 35/12* (2013.01); *H01J 35/165* (2013.01); *G21F 1/06* (2013.01); *H01J 2235/166* (2013.01)

(58) Field of Classification Search
CPC .......... H01J 35/18; H01J 35/112; H01J 35/12; H01J 35/165; H01J 2235/166; G21F 3/00; G21F 7/00; G21F 1/06
USPC ......... 250/505.1, 506.1, 507.1, 515.1, 516.1, 250/517.1, 518.1, 519.1
See application file for complete search history.

(56) References Cited

U.S. PATENT DOCUMENTS

| | | | |
|---|---|---|---|
| 2012/0106713 A1* | 5/2012 | Parker | H01J 35/165 378/140 |
| 2013/0114794 A1* | 5/2013 | Yamamoto | H05G 1/06 378/140 |

FOREIGN PATENT DOCUMENTS

| | | |
|---|---|---|
| KR | 10-2012-0021595 A | 3/2012 |
| KR | 10-1485476 B1 | 1/2015 |
| KR | 10-2016-0024653 A | 3/2016 |
| KR | 10-2016-0051710 A | 5/2016 |

OTHER PUBLICATIONS

Communication dated Dec. 1, 2020, issued by the Korean Patent Office in counterpart Korean Application No. 10-2019-0089615.

* cited by examiner

*Primary Examiner* — Nicole M Ippolito
(74) *Attorney, Agent, or Firm* — Sughrue Mion, PLLC

(57) ABSTRACT

Disclosed is a ceramic shielding apparatus including at least one shield made of a ceramic material and provided inside or outside an X-ray tube to shield radiation; and supports configured to support the shield. According to such a configuration, disadvantages of conventional shielding materials such as lead can be addressed, so that a shield apparatus having excellent shielding properties while being harmless to the human body can be provided.

12 Claims, 7 Drawing Sheets

CERAMIC SHIELDING APPARATUS

CROSS-REFERENCE TO RELATED APPLICATION

This application claims priority to Korean Patent Application No. 10-2019-0089615, filed on Jul. 24, 2019 in the Korean Intellectual Property Office, the disclosure of which is incorporated herein by reference.

BACKGROUND OF THE DISCLOSURE

Field of the Disclosure

The present disclosure relates to a ceramic shielding apparatus, and more particularly, to a ceramic shielding apparatus that is harmless to the human body and exhibits excellent insulating and shielding properties under various conditions.

Description of the Related Art

An X-ray apparatus, which is an apparatus for generating X-rays, consists of an X-ray tube composed of a cathode and anode in a vacuum tube, a high-voltage control for applying high voltage to the X-ray tube, and a cooling device for cooling heat generated in the X-ray tube.

In the case of general X-ray tubes, an insulating oil is configured to have cooling and insulating properties. Accordingly, a metal shielding material, such as lead, is applied to general X-ray tubes, so that a large amount of insulating oil is required and a separate tank for storing a large amount of insulating oil is required.

Meanwhile, in the case of tanks to which lead for radiation shielding is applied, there are disadvantages that the volume is very large and the weight is very heavy due to the material properties of lead. When such a shielding tank is applied to an X-ray tube, efficiency is low, and efficiency is decreased in manufacturing an entire apparatus to be very robust. In addition, shielding parts that are irrelevant to the generation of X-rays are required due to application of a shielding tank to which lead is applied, which causes problems such as increased manufacturing costs.

Accordingly, various studies have been continuously conducted to improve the shielding efficiency of an X-ray apparatus in recent years.

RELATED ART DOCUMENTS

Patent Documents

Korean Patent Application Publication No. 10-2016-0051710
Korean Patent Application Publication No. 10-2012-0021595

SUMMARY OF THE DISCLOSURE

Therefore, the present disclosure has been made in view of the above problems, and it is an object of the present disclosure to provide a ceramic shielding apparatus that is harmless to the human body and exhibits excellent insulating and shielding properties under various conditions.

In accordance with an aspect of the present disclosure, the above and other objects can be accomplished by the provision of a ceramic shielding apparatus, including: at least one shield made of a ceramic material and provided inside or outside an X-ray tube to shield radiation; and supports configured to support the shield.

In addition, the X-ray tube may be provided inside a shielding room to isolate from the outside, and the shield may be in close contact with the shielding room, in a state of being supported by the supports, or may be provided inside the shielding room to surround the X-ray tube.

In addition, the shield may include a plurality of shielding blocks made of the ceramic material; and reinforcing members configured to support a mutually connected state of the plurality of shielding blocks to reinforce shielding ability.

In addition, the supports may be provided as a pair of supports to respectively support a front surface of the shield facing the X-ray tube and a rear surface opposite to the front surface of the shield, and may be made of a plastic material.

In addition, each of the plurality of shielding blocks may include: a block body having a square block shape; at least one connection protrusion protruding from a side of the block body; and at least one connection groove, into which connection protrusions of adjacent block bodies inserted, grooved into another side of the block body.

In addition, connection portions where the plurality of shielding blocks are connected to each other may be sealed with a sealing material as a composite material containing silicone, and the sealing material may at least partially include the ceramic material having radiation-shielding properties.

In addition, guide protrusions including a first guide for guiding the reinforcing members in one direction and a second guide extending in another direction orthogonal to the first guide may respectively protrude from the front surfaces of the shielding blocks facing the X-ray tube and the rear surfaces of the shielding blocks opposite to the front surfaces, and the reinforcing members may be guided along the first guides on the front surfaces of the shielding blocks and the second guides on the rear surfaces of the shielding blocks, thereby being provided in a pair of bar shape to simultaneously support the plurality of shielding blocks.

In addition, the shield may be provided inside the X-ray tube, the shield may include a first shield provided as a base to support a bottom of the X-ray tube; and at least one second shield configured to extend vertically upward from the first shield and to be in close contact with an inner circumferential surface of the X-ray body forming a side thereof of the X-ray tube.

In addition, the X-ray tube may include an anode provided with a transmission-type target where electrons generated from an X-ray source transmits to generate X-rays, and the shield may be provided to surround the X-ray source and provided as side walls of the X-ray tube such that the anode is stacked on the shield.

In addition, the ceramic material may at least partially include bismuth oxide ($Bi_2O_3$) to be molded by heat and pressure.

In accordance with another aspect of the present disclosure, there is provided a ceramic shielding apparatus, including: at least one shield made of a ceramic material to shield radiation generated from an X-ray tube; and supports configured to support the shield, wherein the shield is provided to surround the outside of the X-ray tube or to be supported by an X-ray body inside the X-ray tube, or provided integrally with the X-ray tube.

In addition, the shield may include a plurality of shielding blocks made of the ceramic material and configured to be connected to each other; and reinforcing members configured to support a mutually connected state of the plurality of shielding blocks to reinforce shielding ability, wherein connection portions of the plurality of shielding blocks are sealed with a sealing material as a composite material containing silicone, and the sealing material at least partially includes the ceramic material.

In addition, each of the plurality of shielding blocks may include a block body having a square block shape; at least one connection protrusion protruding from a side of the block body; and at least one connection groove, into which connection protrusions of adjacent block bodies inserted, grooved into another side of the block body.

In addition, guide protrusions including a first guide for guiding the reinforcing members in one direction and a second guide extending in another direction orthogonal to the first guide may respectively protrude from the front surfaces of the shielding blocks facing the X-ray tube and the rear surfaces of the shielding blocks opposite to the front surfaces, and the reinforcing members may be guided along the first guides on the front surfaces of the shielding blocks and the second guides on the rear surfaces of the shielding blocks, thereby being provided in a pair of bar shape to simultaneously support the plurality of shielding blocks.

In addition, the shield may be provided inside the X-ray tube, the shield including a first shield provided as a base to support a bottom of the X-ray tube; and at least one second shield configured to extend vertically upward from the first shield and to be in close contact with an inner circumferential surface of the X-ray body forming a side thereof of the X-ray tube.

In addition, the X-ray tube may include an anode provided with a transmission-type target where electrons generated from an X-ray source transmits to generate X-rays, and the shield may be provided to surround the X-ray source and provided as side walls of the X-ray tube such that the anode is stacked on the shield.

In addition, the ceramic material may at least partially include bismuth oxide ($Bi_2O_3$) to be molded by heat and pressure.

In addition, the X-ray tube may be provided inside a shielding room to isolate from the outside, and the shield may be supported by the supports, may be in close contact with an inner wall of the shielding room or may be provided inside the shielding room to surround the X-ray tube, and may at least partially include bismuth oxide ($Bi_2O_3$) and a conductive metal powder to be molded by heat and pressure.

In addition, the supports may be made of a plastic material, and may be in close contact with at least one surface of the shield or may be provided integrally with the X-ray tube.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Hereinafter, preferred embodiments of the present disclosure will be described with reference to the accompanying drawings. However, the spirit of the present disclosure is not limited to the embodiments, and the spirit of the present disclosure may be proposed differently by adding, changing, and deleting the elements constituting the embodiments, which is also within the spirit of the present disclosure.

Figure 1:
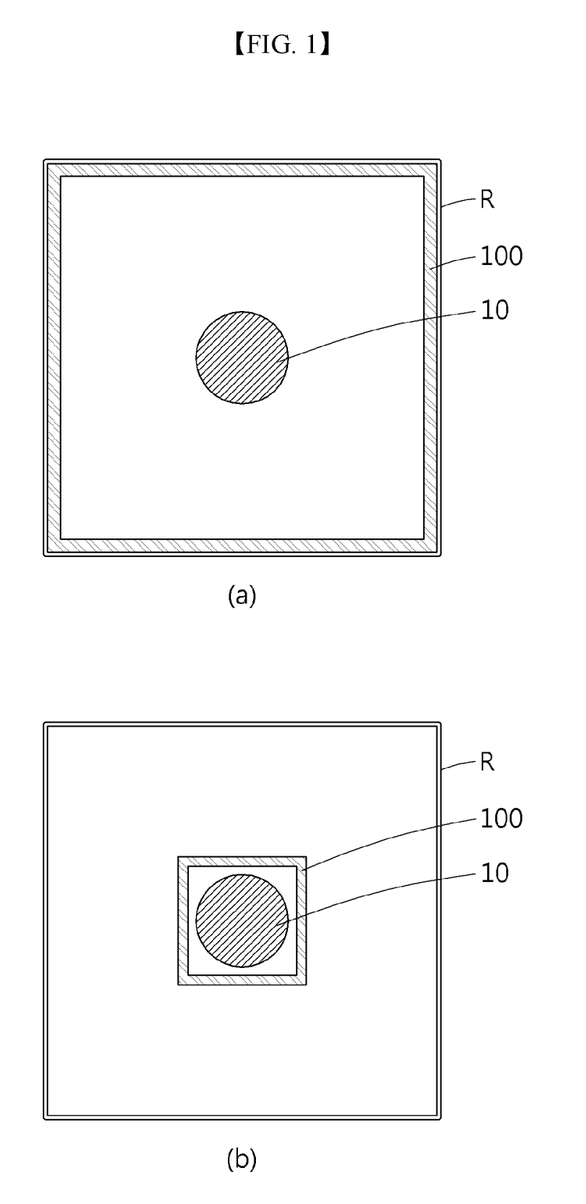
FIG. 1 is a plan view schematically illustrating a ceramic shielding apparatus provided outside of an X-ray tube according to a preferred first embodiment of the present disclosure.
Figure 2:
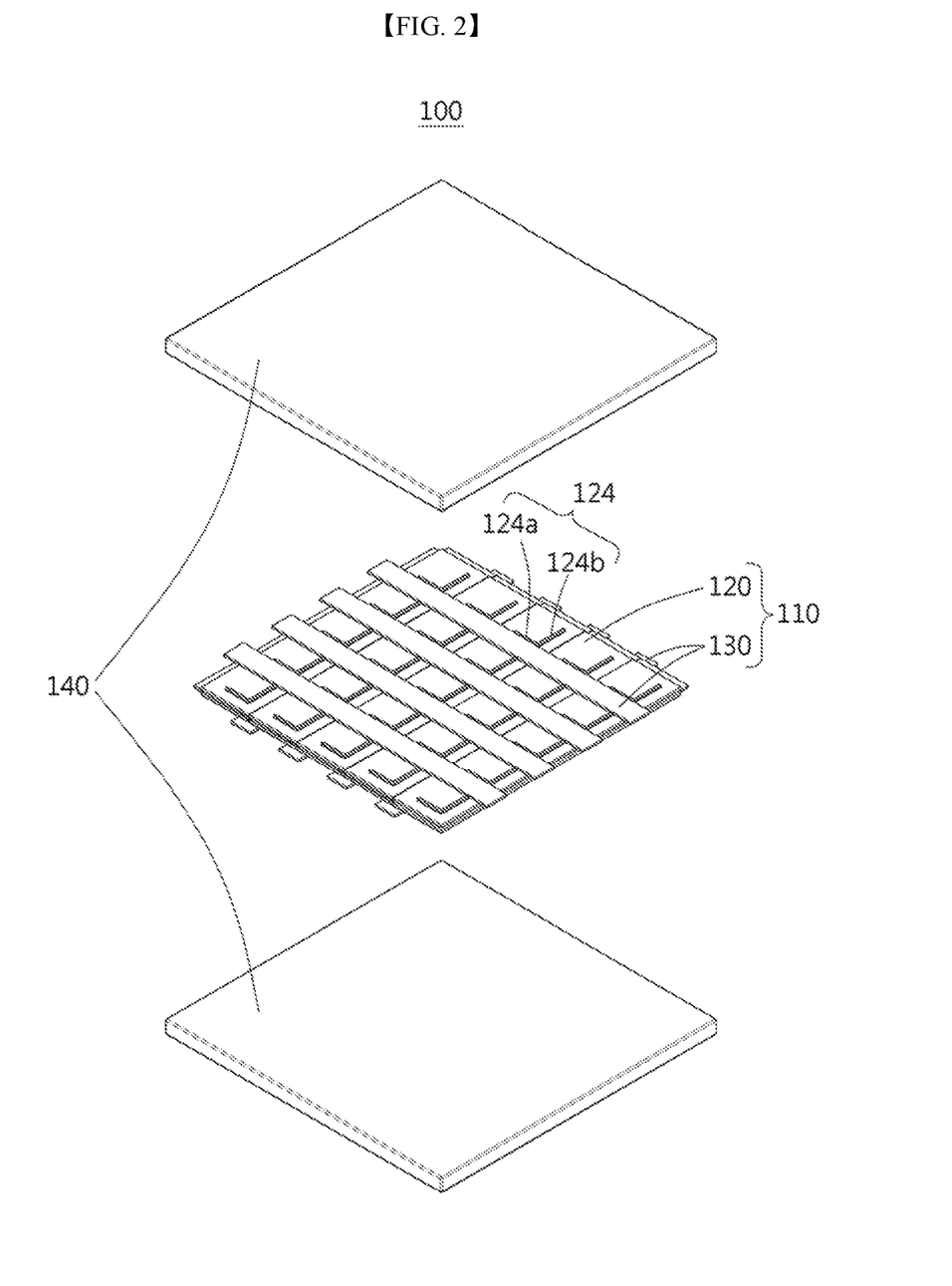
FIG. 2 illustrates a schematically exploded perspective view of the ceramic shielding apparatus shown in FIG. 1.

Referring to FIGS. 1 and 2, a ceramic shielding apparatus 100 according to a preferred first embodiment of the present disclosure includes a shield 110 and supports 140.

For reference, the ceramic shielding apparatus 100 described in the first embodiment is installed in a shielding room R for separating an X-ray tube 10 from the outside and is provided outside of the X-ray tube 10 as shown in (a) and (b) of FIG. 1. Here, the ceramic shielding apparatus 100 may be installed to be in close contact with inner walls of the shielding room R as shown in (a) of FIG. 1, or may be installed to be spaced from inner walls of the shielding room R and to surround the X-ray tube 10 in a position adjacent to the X-ray tube 10 as shown in (b) of FIG. 1. An installation position of the ceramic shielding apparatus 100 is not limited to those illustrated in FIG. 1 and may be installed at various position outside of the X-ray tube 10 so long as radiation generated from the X-ray tube 10 can be shielded.

The shield 110 is provided outside of the X-ray tube 10 to shield radiation due to X-ray generation from the X-ray tube 10. The shield 110 is made of a ceramic material having insulating properties and radiation-shielding properties, thereby serving to shield radiation generated from the X-ray tube 10. The ceramic material will be described in more detail below.

The shield 110 according to the first embodiment includes shielding blocks 120 and reinforcing members 130 as shown in FIG. 2.

Figure 3:
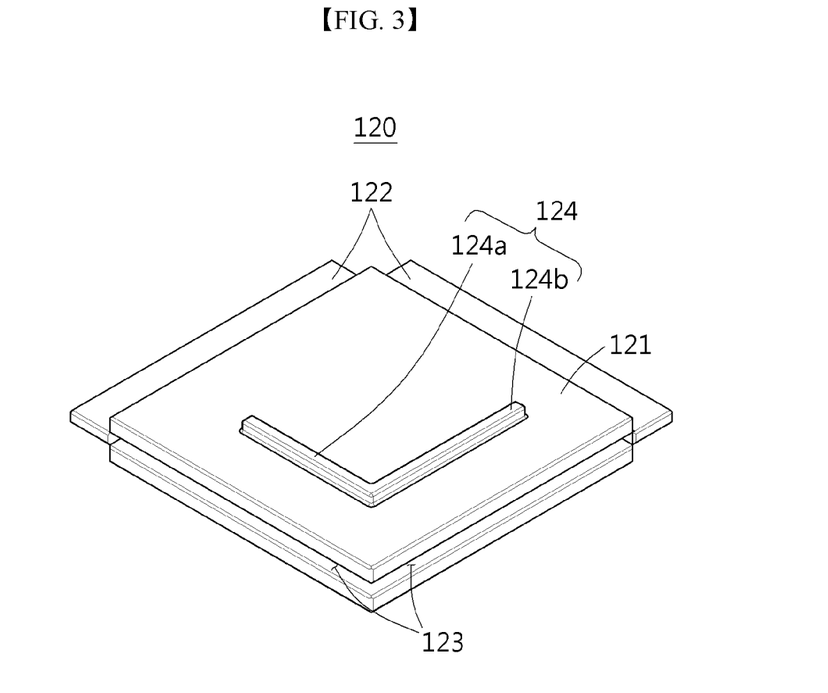
FIG. 3 illustrates a schematically enlarged perspective view of each of shielding blocks shown in FIG. 2.

The plurality of shielding blocks 120 are provided to surround the X-ray tube 10 at a position spaced apart from the X-ray tube 10. Each of the shielding blocks 120 includes a block body 121, connection protrusions 122 and connection grooves 123 as shown in FIG. 3 and is made of a ceramic material.

The block body 121 has a square block shape. The block body 121 is formed of a ceramic material. The size and shape of the block body 121 are not limited to those shown in FIG. 3 and may naturally have various polygonal shapes.

At least one of the connection protrusions 122 protrudes from a side of the block body 121. In the present embodiment, it is exemplified that the connection protrusions 122 respectively protrude from two adjacent side surfaces of the block body 121 having a square block shape. That is, two connection protrusions 122 are provided to respectively protrude from two of four sides of the block body 121.

At least one connection groove 123 is provided in a shape of being grooved from sides of the block body 121, and the connection protrusions 122 protruded from adjacent block bodies 121 are inserted into the at least one connection groove 123. In the present embodiment, it is exemplified that two sides, which are not provided with the connection protrusions 122, of four sides of the block body 121 having a square block shape are provided with the connection groove 123.

Figure 4:
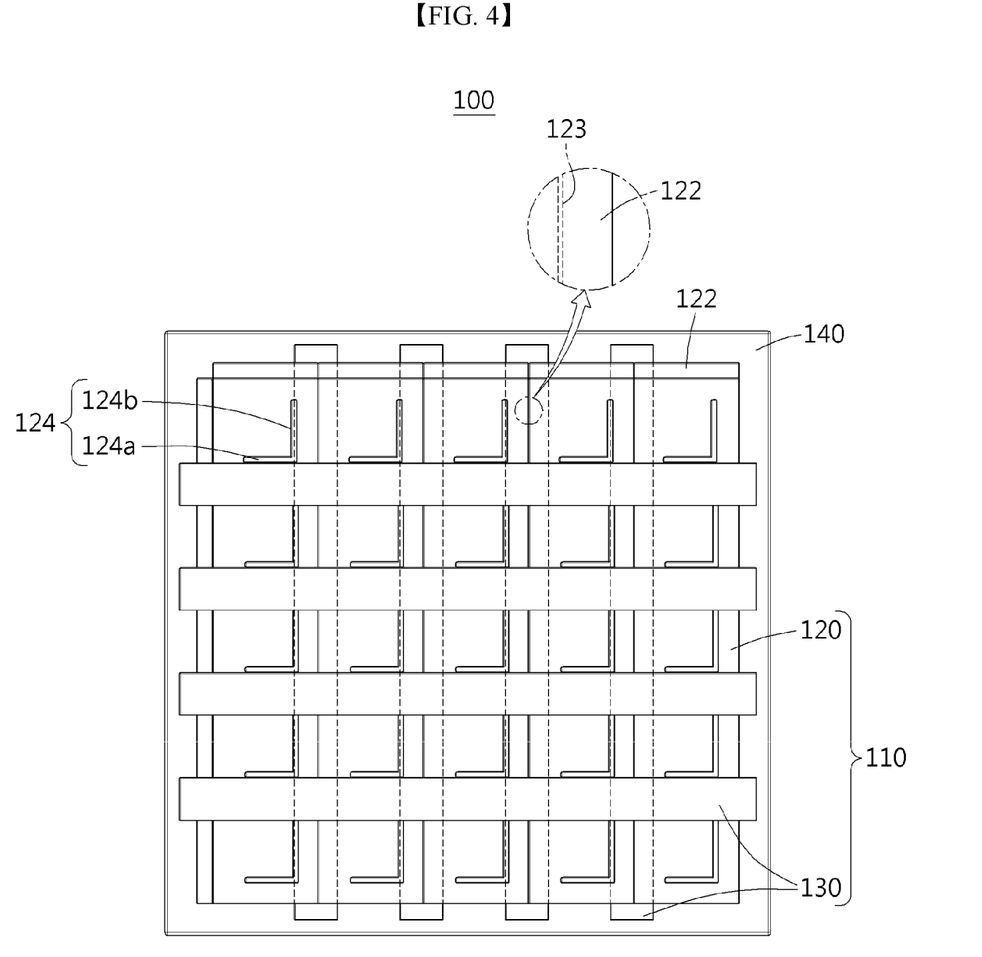
FIG. 4 illustrates a schematic plan view of the ceramic shielding apparatus shown in FIG. 2.

When the plurality of block bodies 121 are arranged side by side to be adjacent to each other according to such a configuration, as shown in FIG. 4, the connection protrusions 122 are inserted into the connection grooves 123 adjacent thereto, so that the plurality of block bodies 121 may be connected to each other in the form of a keyway.

Here, connection portions, where the plurality of block bodies 121 are connected to each other, may be sealed by being filled with a sealing material (not shown) as a composite material including silicone. More particularly, when the connection protrusions 122 protruding from the block body 121 are inserted into the connection grooves 123 of adjacent block bodies 121, the connection protrusions 122 are inserted into the connection grooves 123 in a state wherein the connection grooves 123 are filled with a silicone sealing material, so that the connection portions are mutually sealed.

According to such a configuration, gaps between the plurality of shielding blocks 120 may be sealed by silicone. In addition, durability may be increased by finishing, with silicone, gaps between the plurality of shielding blocks 120 that are easily broken due to the properties of a ceramic material. Meanwhile, when a sealing material including silicone contains a portion of a ceramic material constituting the shield 110, the shielding ability may be further improved.

The reinforcing members 130 are made of the same eco-friendly, highly insulating, and shieldable ceramic material as the shielding blocks 120, thereby supporting the connection state of the plurality of shielding blocks 120 and reinforcing the shielding ability thereof. A pair of reinforcing members 130 may be provided in a direction crossing front and rear surfaces of each of the shielding blocks 120 to support the plurality of shielding blocks 120 as shown in FIG. 2. In addition, the reinforcing members 130 may have a bar shape extending in a longitudinal direction to simultaneously support the plurality of shielding blocks 120. Here, the front surface of the shielding blocks 120 faces the X-ray tube 10, and the rear surface of the shielding blocks 120 faces the front surfaces of the shielding blocks 120.

Insertion of the reinforcing members 130 is guided by guide protrusions 124 protruding from front and rear surfaces of the shielding blocks 120. More particularly, the guide protrusions 124 respectively protrude from front and rear surfaces of the block body 121, i.e., each of the guide protrusions 124 includes a first guide 124a extending from front and rear surfaces of each of the shielding blocks 120; and a second guide 124b extending in a direction orthogonal from one end of the first guide 124a. In the embodiment, it is exemplified that the first and second guides 124a and 124b of the guide protrusions 124 are connected to each other, so that the guide protrusions 124 have an "L" shape, but the present disclosure is not limited thereto.

The reinforcing members 130 are guided in one direction along the first guides 124a of the guide protrusions 124 protruding from the front surface of the shielding blocks 120 to support the front surface of the plurality of shielding blocks 120. In addition, the reinforcing members 130 are guided in another direction, which is orthogonal to the direction, along the second guides 124b of the guide protrusions 124 protruding from the rear surface of the shielding blocks 120 to support the rear surface of the plurality of shielding blocks 120. Accordingly, a pair of reinforcing members 130 support front and rear surfaces of the plurality of shielding blocks 120 in a direction perpendicular to each other, thereby supporting the connected state of the plurality of shielding blocks 120. In addition, the pair of reinforcing members 130 are made of the same ceramic material as that of the shielding blocks 120, thereby increasing a radiation shielding ratio while supporting the front and rear surfaces of the shielding blocks 120.

The supports 140 support the shield 110. More particularly, the supports 140 are in close contact with front and rear surfaces of the plurality of shielding blocks 120 that are connected to each other and are supported by the reinforcing members 130 as shown in FIG. 2, thereby supporting the plurality of shielding blocks 120. The supports 140 may be formed of a PVC plastic material, and a pair of supports 140 may be provided to be in close contact with the front and rear surfaces of the shielding blocks 120.

Figure 5:
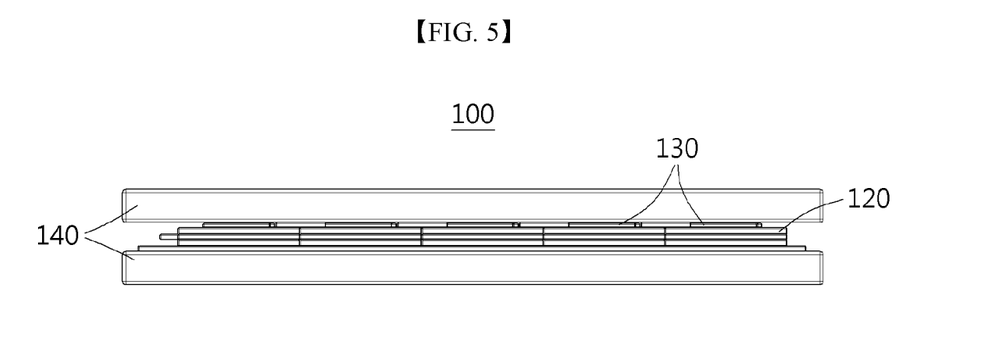
FIG. 5 illustrates a schematic side view of the ceramic shielding apparatus shown in FIG. 2.

According to such a configuration, the shielding blocks 120 and the reinforcing members 130 are disposed between the pair of supports 140 as shown in FIG. 5. Here, the plurality of shielding blocks 120 disposed between the pair of supports 140 are connected to each other by coupling force between the connection protrusions 122 and the connection grooves 123 and the connected state is firmly supported by the reinforcing members 130.

For reference, the number of the plurality of shielding blocks 120 is not limited to the illustrated example and may be variously changed according to the size of the shielding room R as shown in FIG. 1. That is, the number of the shielding blocks 120 may be changed according to various conditions and constructed in a customized form.

In addition, it is exemplified that the shield 110 described in the present disclosure has a thickness of about 15 mm or less, and the supports 130 have a thickness of about 20 mm. For reference, as experimental results of a radiation energy shielding ratio of the shield 110 against a commonly applied X-ray tube 10 for CT scan, the shield 110 having a weight of about 120 to 150 kg and a thickness of 8 mm exhibited a shielding ratio of about 95%, and the shield 110 having a weight of about 120 to 150 kg and a thickness of 12 mm exhibited a shielding ratio of about 97%. The thickness of the shield 110 is not specifically limited and may be changed according to conditions such as the type of the X-ray tube 10, the shielding room R, and the like. For example, when a very small amount of radiation shielding, which is lower than that in CT scan, is required, the shield 110 having a weight of only about 120 kg and a thickness of 2 mm may realize a shielding ratio close to 100%. Accordingly, since the thickness of the shield 110 is provided in a range of about 15 mm, a sufficient shielding ratio may be simply realized.

Figure 6:
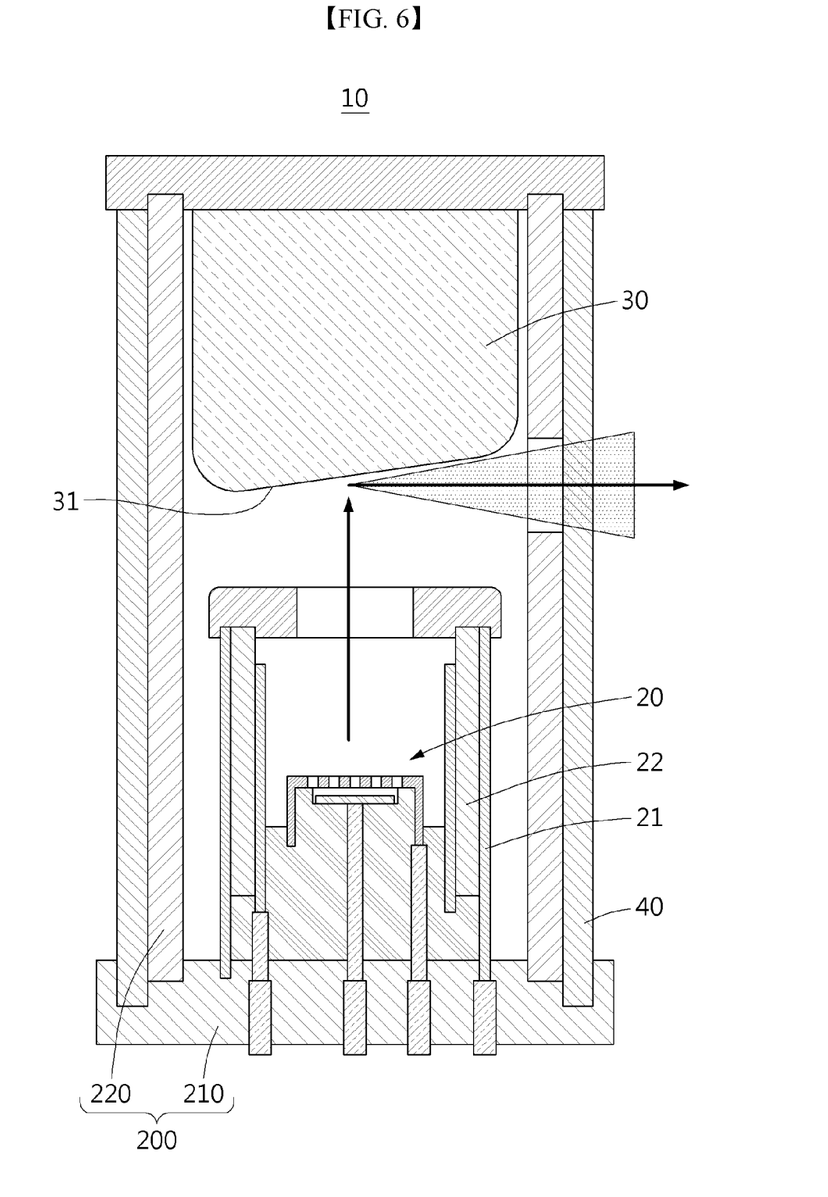
FIG. 6 illustrates a schematic sectional view of a ceramic shielding apparatus according to a second embodiment of the present disclosure.

Referring to FIG. 6, a sectional view of a ceramic shielding apparatus 200 according to the second embodiment of the present disclosure is schematically illustrated. As shown in FIG. 6, the ceramic shielding apparatus 200 according to the second embodiment is provided in the X-ray tube 10 to shield radiation. For this, the ceramic shielding apparatus 200 incudes the first and second shields 210 and 220.

For reference, the X-ray tube 10 illustrated in the second embodiment includes an X-ray source 20 configured to generate electrons for X-ray generation, an anode 30 configured to generate X-rays when struck by electrons generated from the X-ray source 20, and an X-ray body 40 configured to support the X-ray source 20 and the anode 30.

Here, the X-ray source 20 may be isolated and supported by partition walls 21, and an insulating material is filled between the partition walls 21 to electrically protect the X-ray source 20. In addition, the anode 30 is provided with an inclined target 31 so that generated X-rays are reflected by the target 31 of the main body 40 and guided to the outside. Since such a configuration of the reflective X-ray tube 10 is not the gist of the present disclosure, detailed description and illustration thereof are omitted.

A first shield 210 is provided inside the X-ray tube 10 and is provided as a bottom surface, i.e., a base, of the X-ray tube 10 for supporting the X-ray source 20. That is, the first shield 210 is provided to support the X-ray source 20 and replaces the role of a conventional base for supporting the X-ray source 20. However, the present disclosure is not limited thereto, and a modified example wherein the X-ray source 20 is supported by a separate base (not shown) and the first shield 210 is provided to be in close contact with the base (not shown) is allowed.

Such a first shield 210 is exemplified as being molded and manufactured to have a plate shape such as a disk as shown in FIG. 6, but the present disclosure is not limited thereto. That is, the first shield 210 may be manufactured in various shapes, such as a polygonal plate and a cylindrical shape, depending upon the conditions of the X-ray source 20 and shielding conditions, and a modified example wherein a plurality of shielding blocks are provided and mutually assembled as in the first embodiment is allowed.

The second shield 220 extends vertically upward from the first shield 210 and is provided along an inner circumferential surface of the X-ray body 40 forming a side of the X-ray tube 10. The second shield 220 may be molded in a cylindrical shape to be in close contact with the inner circumferential surface of the X-ray body 40 having a cylindrical shape. The shape of the second shield 220 may also be variously modified according to conditions of the X-ray source 20, and a modified example including a plurality of shielding blocks, as in the first embodiment, is allowed.

That is, both the first and second shields 210 and 220 are illustrated and exemplified as having a single disk and cylindrical shape, but the present disclosure is not limited thereto.

For reference, the second shield 220 is supported by the X-ray body 40. That is, the X-ray body 40 of the X-ray tube 10 serves as a support for supporting the shield including the first and second shields 210 and 220.

Meanwhile, it is natural that the shape of the second shield 220 is not limited to the illustrated embodiment. That is, various modified examples are allowed. For example, a plurality of second shields 220 may be provided to be in close contact with each other or to be spaced apart from each other at a predetermined interval and to be in close contact with an inner circumferential surface of the X-ray body 40.

Although not shown in detail, the X-ray body 40 of the X-ray tube 10 is provided with a window (not shown) through which X-rays guided by the target 31 of the anode 30 pass, and the first and second shields 210 and 220 are provided not to interfere with the window (not shown). Accordingly, the first and second shields 210 and 220 may shield radiation except for X-rays emitted to the outside through the window (not shown).

Figure 7:
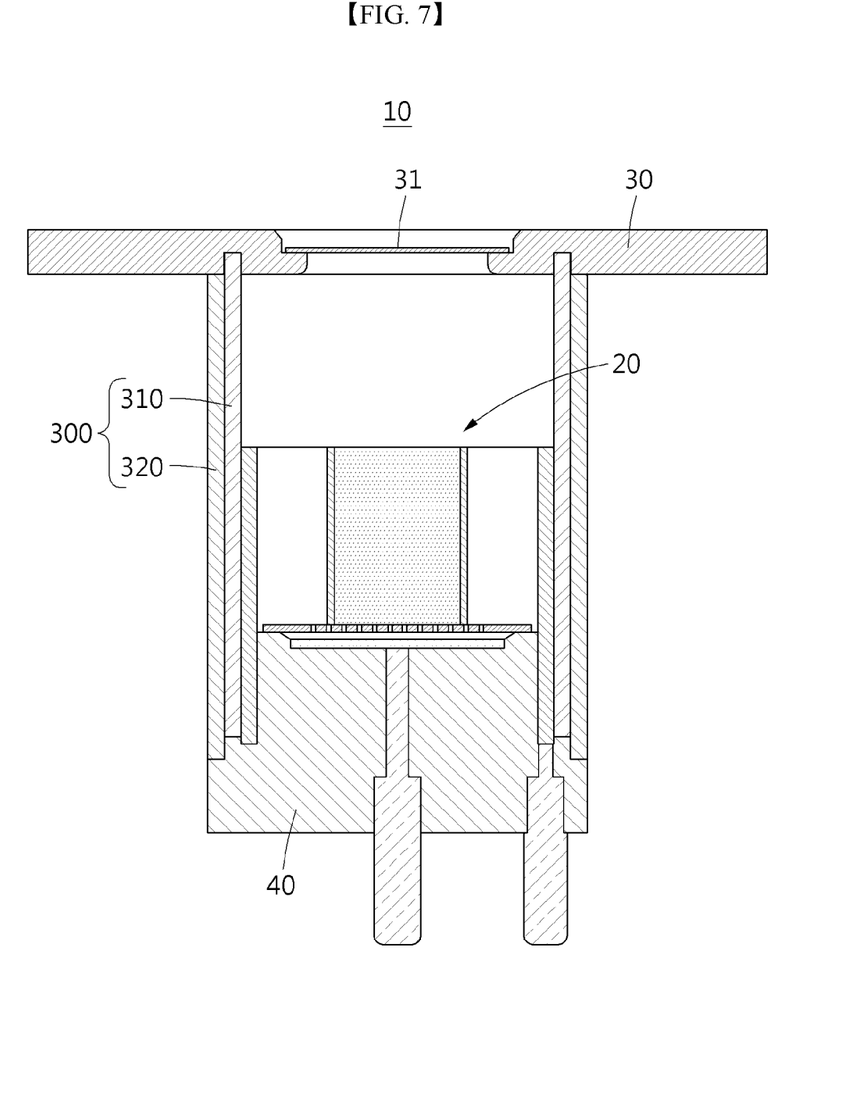
FIG. 7 illustrates a schematic sectional view of a ceramic shielding apparatus according to a third embodiment of the present disclosure.

FIG. 7 schematically illustrates a ceramic shielding apparatus 300 according to a preferred third embodiment of the present disclosure.

Referring to FIG. 7, the ceramic shielding apparatus 300 according to the third embodiment is also provided inside an X-ray tube 10 to shield radiation.

Here, the X-ray tube 10 according to the third embodiment is a transmission type different from the reflective X-ray tube 10 according to the second embodiment illustrated in FIG. 6. The transmission-type X-ray tube 10 shown in FIG. 7 is provided with an anode 30 including a target 31 that faces an X-ray source 20, thereby emitting X-rays to the outside through the target 31. The X-ray source 20 is supported by a main body 40.

The ceramic shielding apparatus 300 according to the third embodiment includes first and second shields 310 and 320. Here, both the first and second shields 310 and 320 extend vertically upward from the main body 40 that supports the X-ray source 20, and are in close contact with each other. Accordingly, the first and second shields 310 and 320 have a cylindrical shape that surrounds and shields the X-ray source 20, thereby doubly shielding radiation.

The first and second shields 310 and 320 extend from the X-ray body 40, which is a kind of base, to surround and protect the X-ray source 20, and the anode 30 is stacked on the first and second shields 310 and 320. Accordingly, the first and second shields 310 and 320 are provided as a side wall of the X-ray tube 10 and, simultaneously, serve to shield radiation.

More particularly, the transmission-type X-ray tube 10 shown in FIG. 7 does not require a separate window for X-ray emission on a side wall thereof, so that the first and second shields 310 and 320 made of an eco-friendly cylindrical ceramic material may be utilized as side walls of the X-ray tube 10. That is, the plurality of shields 310 and 320 made of a ceramic material may shield radiation multiple times while supporting the X-ray source 20 and the anode 30, without provision of a separate side wall to the X-ray source 20.

Accordingly, since the shields 310 and 320 having shielding and insulating properties are embedded in the transmission-type X-ray tube 10, an overall size, volume, and weight may be reduced and there are economic advantages according to manufacturing cost reduction. For reference, a modified example is allowed, for example, the transmission-type X-ray tube 10 may also be provided with a separate side wall and the first and second shields 310 and 320 may be supported by the side wall (not shown).

Figure 8:
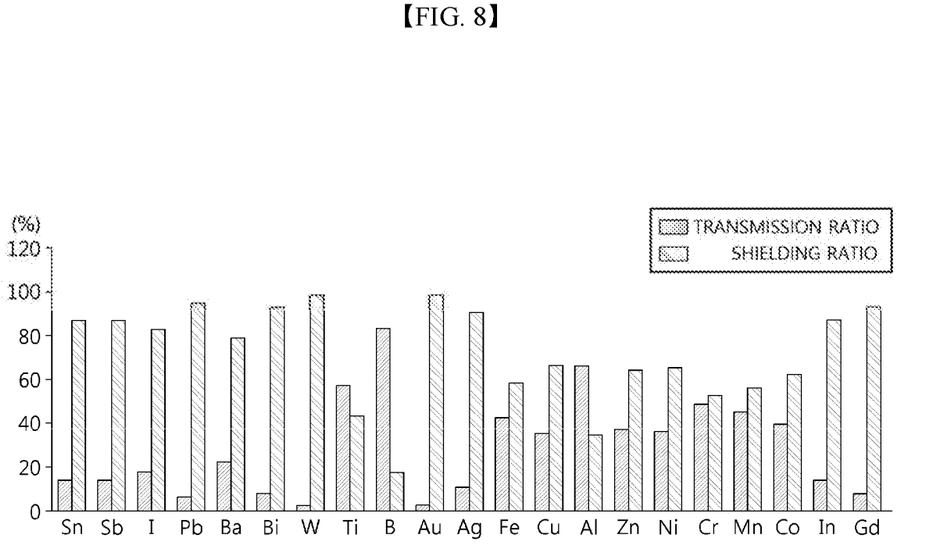
FIG. 8 illustrates comparison results of ceramic material type-dependent transmission and shielding ratios of ceramic shielding apparatuses according to the present disclosure.

FIG. 8 illustrates comparison results of ceramic material type-dependent transmission and shielding ratios of the ceramic shielding apparatuses 100, 200, and 300 according to the present disclosure described above.

Referring to FIG. 8, it can be confirmed that bismuth (Bi) has transmission and shielding ratios similar to those of lead (Pb) that has been mainly used as a shielding material for an X-ray tube 10. Accordingly, it is exemplified that a ceramic material applied to the ceramic shielding apparatuses 100, 200, and 300 according to the first to third embodiments at least partially includes bismuth oxide ($Bi_2O_3$) that has the most similar density to lead and, accordingly, has strong insulating properties.

Meanwhile, the shield 110 applied to the shielding room R as in the first embodiment may be made to have various compositions including bismuth oxide and a portion of other materials. More particularly, the shield 110 in close contact with the shielding room R that is spaced apart from the X-ray tube 10 requires low insulating properties against the X-ray tube 10 compared to those according to the second and third embodiments provided inside the X-ray tube 10. Accordingly, the shield 110 according to the first embodiment is made of bismuth oxide along with a metal powder having superior shielding ability to lead (Pb) and conductivity, so that improvement of mechanical strength and shielding ability or functions such as thickness control may be provided.

In addition, a sealing material (not shown) filling connection portions between the plurality of shielding blocks 120 according to the first embodiment may be a composite composed of various compositions including bismuth oxide along with silicone. Accordingly, the sealing material (not shown) filled between the plurality of shielding blocks 120 to connect to each other may have high filling and adhesive properties and, simultaneously, shielding capability.

For reference, when the shields 210, 220, 310, and 320 are provided inside the X-ray tube 10 as in the second and third embodiments, only insulating and shielding properties are required. Accordingly, the shields 210, 220, 310, and 320 may be made of pure bismuth oxide.

The shields 120, 210, 220, 310, and 320 described in the present disclosure may be made by ceramicizing a ceramic material that partially or entirely includes a bismuth powder having high insulating and shielding properties to withstand a high-temperature vacuum brazing process. That is, the ceramic material according to the present disclosure is subjected to a process of sintering at high temperature because it is made by homogeneously compression-molding a bismuth oxide powder under high pressure.

As such, since a material having insulating and shielding properties, such as a bismuth oxide power, is at least partially included in the shields and, accordingly, the shields may be molded using heat and pressure, the shields may be manufactured to have desired shapes corresponding to X-ray tubes 10 under various conditions. Accordingly, the shields may be provided inside/outside a conventional shielding room R or X-ray tube 10 without the need to secure an unnecessary space for shielding, enabling realization of a compact shield.

In accordance with the present disclosure having the aforementioned configuration, first, an eco-friendly ceramic shielding apparatus, instead of lead harmful to the human body, is provided. Accordingly, the ceramic shielding apparatus according to the present disclosure is harmless to the human body and can be easily manufactured and installed.

Second, since a plurality of shielding blocks are connected to each other and are installed inside a shielding room, there is an advantage that even one worker can construct shielding in a customized form in response to various sizes and conditions.

Third, connection portions of the plurality of shielding blocks are sealed using a sealing material containing silicone and are supported by supports made of a plastic material, so that mechanical properties can be improved. In addition, since the sealing material partially contains a ceramic material along with silicone, shielding properties can be added.

Fourth, the shielding apparatus made of a ceramic material can be installed inside an X-ray tube, so that separate alignment is unnecessary and a compact structure having excellent shielding properties can be provided.

Fifth, the shielding apparatus is installed instead of a side wall of a transmission-type X-ray tube not requiring a window, so that size reduction and high economic efficiency can be accomplished.

Sixth, the thickness and strength of a shield can be improved using various compositions such as a composition prepared by adding a metal powder to a ceramic material, so that the shield can exhibit various functions and thus efficiency increase can be expected.

Although the present disclosure has been described above with reference to the embodiments of the present disclosure, those skilled in the art may variously modify and change the present disclosure without departing from the spirit and scope of the present disclosure as set forth in the claims below.

Description of Symbols

10: X-ray tube
20: X-ray source
30: anode
40: main body
100, 200, 300: ceramic shielding apparatus
110: shield
120: shielding block
130: reinforcing member
140: support
210, 310: first shield
220, 320: second shield

What is claimed is:

1. A ceramic shielding apparatus, comprising:
   at least one shield made of a ceramic material and provided inside or outside an X-ray tube to shield radiation; and
   supports configured to support the shield,
   wherein the X-ray tube is provided inside a shielding room to isolate from the outside, and the shield is in close contact with the shielding room in a state of being supported by the supports, or is provided inside the shielding room to surround the X-ray tube, and
   wherein the shield comprises:
   a plurality of shielding blocks made of the ceramic material; and
   reinforcing members configured to support a mutually connected state of the plurality of shielding blocks to reinforce shielding ability.

2. The ceramic shielding apparatus according to claim 1, wherein the supports are provided as a pair of supports to respectively support a front surface of the shield facing the X-ray tube and a rear surface opposite to the front surface of the shield, and are made of a plastic material.

3. The ceramic shielding apparatus according to claim 1, wherein each of the plurality of shielding blocks comprises:
   a block body having a square block shape;
   at least one connection protrusion protruding from a side of the block body; and
   at least one connection groove, into which connection protrusions of adjacent block bodies inserted, grooved into another side of the block body.

4. The ceramic shielding apparatus according to claim 1, wherein connection portions where the plurality of shielding blocks are connected to each other are sealed with a sealing material as a composite material containing silicone, and
   the sealing material at least partially comprises the ceramic material having radiation-shielding properties.

5. The ceramic shielding apparatus according to claim 1, wherein guide protrusions comprising a first guide for guiding the reinforcing members in one direction and a second guide extending in another direction orthogonal to the first guide respectively protrude from the front surfaces of the shielding blocks facing the X-ray tube and the rear surfaces of the shielding blocks opposite to the front surfaces, and
   the reinforcing members are guided along the first guides on the front surfaces of the shielding blocks and the second guides on the rear surfaces of the shielding blocks, thereby being provided in a pair of bar shape to simultaneously support the plurality of shielding blocks.

6. The ceramic shielding apparatus according to claim 1, wherein the ceramic material at least partially comprises bismuth oxide ($Bi_2O_3$) to be molded by heat and pressure.

7. A ceramic shielding apparatus, comprising:
at least one shield made of a ceramic material to shield radiation generated from an X-ray tube; and
supports configured to support the shield,
wherein the shield is provided to surround the outside of the X-ray tube or to be supported by an X-ray body inside the X-ray tube, or provided integrally with the X-ray tube,
wherein the shield comprises:
a plurality of shielding blocks made of the ceramic material and configured to be connected to each other; and
reinforcing members configured to support a mutually connected state of the plurality of shielding blocks to reinforce shielding ability,
wherein connection portions of the plurality of shielding blocks are sealed with a sealing material as a composite material containing silicone, and
wherein the sealing material at least partially comprises the ceramic material.

8. The ceramic shielding apparatus according to claim 7, wherein each of the plurality of shielding blocks comprises:
a block body having a square block shape;
at least one connection protrusion protruding from a side of the block body; and
at least one connection groove, into which connection protrusions of adjacent block bodies inserted, grooved into another side of the block body.

9. The ceramic shielding apparatus according to claim 7, wherein guide protrusions comprising a first guide for guiding the reinforcing members in one direction and a second guide extending in another direction orthogonal to the first guide respectively protrude from the front surfaces of the shielding blocks facing the X-ray tube and the rear surfaces of the shielding blocks opposite to the front surfaces, and
the reinforcing members are guided along the first guides on the front surfaces of the shielding blocks and the second guides on the rear surfaces of the shielding blocks, thereby being provided in a pair of bar shape to simultaneously support the plurality of shielding blocks.

10. The ceramic shielding apparatus according to claim 7, wherein the ceramic material at least partially comprises bismuth oxide ($Bi_2O_3$) to be molded by heat and pressure.

11. The ceramic shielding apparatus according to claim 7, wherein the X-ray tube is provided inside a shielding room to isolate from the outside, and
the shield is supported by the supports, is in close contact with an inner wall of the shielding room or is provided inside the shielding room to surround the X-ray tube, and at least partially comprises bismuth oxide ($Bi_2O_3$) and a conductive metal powder to be molded by heat and pressure.

12. The ceramic shielding apparatus according to claim 7, wherein the supports are made of a plastic material, and are in close contact with at least one surface of the shield or are provided integrally with the X-ray tube.

\* \* \* \* \*